(12) United States Patent
Kong

(10) Patent No.: US 9,810,608 B2
(45) Date of Patent: *Nov. 7, 2017

(54) TRANSPARENT FROZEN SOIL AND PREPARATION METHOD AND APPLICATION THEREOF

(71) Applicant: Hohai University, Nanjing, Jiangsu (CN)

(72) Inventor: Gangqiang Kong, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 269 days.

This patent is subject to a terminal disclaimer.

(21) Appl. No.: 14/763,536

(22) PCT Filed: May 27, 2014

(86) PCT No.: PCT/CN2014/078525
§ 371 (c)(1),
(2) Date: Jul. 27, 2015

(87) PCT Pub. No.: WO2015/165139
PCT Pub. Date: Nov. 5, 2015

(65) Prior Publication Data
US 2016/0216247 A1    Jul. 28, 2016

(30) Foreign Application Priority Data

Apr. 30, 2014  (CN) .......................... 2014 1 0177674
Apr. 30, 2014  (CN) .......................... 2014 1 0179108
Apr. 30, 2014  (CN) .......................... 2014 1 0180405

(51) Int. Cl.
*G01N 1/28* (2006.01)
*G01N 3/22* (2006.01)
(Continued)

(52) U.S. Cl.
CPC .......... *G01N 1/28* (2013.01); *C08F 214/262* (2013.01); *C08F 224/00* (2013.01); *F42D 3/00* (2013.01);
(Continued)

(58) Field of Classification Search
CPC ...... G01N 1/28; G01N 33/227; G01N 1/2806; G01N 1/38; G01N 1/42; G01N 33/24;
(Continued)

(56) References Cited

U.S. PATENT DOCUMENTS

2016/0244547 A1* 8/2016 Jagannathan ............ B01J 3/008

FOREIGN PATENT DOCUMENTS

CN   1560557     1/2005
CN   102230856   11/2011

OTHER PUBLICATIONS

Derwent Abstract of RU 236485 C1, 2010.*
(Continued)

*Primary Examiner* — Nicole Buie-Hatcher
(74) *Attorney, Agent, or Firm* — Rankin, Hill & Clark LLP

(57) ABSTRACT

The present invention discloses a transparent frozen soil, which is prepared from a fluorine-containing polymer, ice particles and a colorless pore fluid by steps of preparing materials, blending, vacuuming, and freezing. The fluorine-containing polymer is poly[4,5-difluoro-2,2bis(trifluoromethyl)-1,3-dioxole-co-tetrafluoroethylene], with the refractive index of 1.31, and are particles with the particle diameter of 0.25-2.0 mm, and the density of 2.1-2.3 g/cm$^3$. The present invention also provides the application of the above transparent frozen soil in the frozen soil directional blasting model test and the frozen soil road embankment model thaw-slumping test. The transparent frozen soil prepared by the present invention can well simulate the prop-
(Continued)

erties of natural transparent frozen sandy soil, is effectively used in model tests in the geotechnical engineering, with accurate measurement results, and can realize the visualization of the internal deformation of the soil body, and it is low in the expense, and simple in the operation.

8 Claims, 1 Drawing Sheet

(51) Int. Cl.
    *C08F 224/00*     (2006.01)
    *C08F 214/26*     (2006.01)
    *F42D 3/00*     (2006.01)
    *G01N 1/38*     (2006.01)
    *G01N 1/42*     (2006.01)
    *G01N 33/24*     (2006.01)
    *H04N 7/18*     (2006.01)
    *G01N 33/22*     (2006.01)

(52) U.S. Cl.
    CPC ............ *G01N 1/2806* (2013.01); *G01N 1/38* (2013.01); *G01N 1/42* (2013.01); *G01N 33/227* (2013.01); *G01N 33/24* (2013.01); *H04N 7/181* (2013.01)

(58) Field of Classification Search
CPC ...... C08F 224/00; C08F 214/262; F24D 3/00; H04N 7/181
See application file for complete search history.

(56) References Cited

OTHER PUBLICATIONS

Machine translation fo CN 102230856 A, Jun. 2017.*
International Search Report and Written Opinion of PCT/CN2014/78525 dated Jan. 28, 2015, 11 pages.
"Study on Frozen Soil Blasting Crater and Model Test Of Frozen Soil Blastability", Ma Qinyong. Journal of China Coal Society, 1997, 22(3): 288-293 (w/ English Abstract).
"Preliminary Study on Blasting Parameters for Shaft Excavation in Frozen Soil", Zong Qi, Yang Lujun, Engineering blasting, 1999, 5(2): 25-29 (w/ English Abstract).
"Study of Smooth Blasting in Frozen Soil of the Shaft by Simulation", Jiang Yusong, Journal of Huainan Institute of Technology, 2001, 21(4): 31-34 (w/ English Abstract).
"A Study on Blasting Tests and Methods for Permafrost and Artificially Frozen Soils", Ma Qinyong, Journal of Civil Engineering, 2004, 37(9): 75-78 (w/ English Abstract).

* cited by examiner

TRANSPARENT FROZEN SOIL AND PREPARATION METHOD AND APPLICATION THEREOF

TECHNICAL FIELD

The present invention relates to a transparent soil, particularly relates to a transparent frozen soil and preparation method and application thereof.

BACKGROUND ART

In model tests in the aspect of the geotechnical engineering, the studies on the internal transformation law and mechanism of soil bodies are of great significance on the research of the problem inherence of the geotechnical engineering. Particularly, the area of perennial frozen soil, seasonal frozen soil and temporary frozen soil regions on earth approximately accounts for 50% of the land area, wherein the distribution area of perennial frozen soil is 35,000,000 km$^2$, approximately accounting for 20% of the land area. Frozen soil is a soil body extremely sensitive to the temperature, along with the rise of the temperature, its strength obviously reduces, and the strength after the soil body thaws reduces by a geometry order-of-magnitude relative to that while in freezing. The results of related studies show that, hilly areas of the abdominal zones of perennial frozen soil regions in Qinghai-Tibet Plateau and the like are all possible to form thaw slumping on the sloping land greater than 3° in its thawing process. When the surface layer frozen soil thaws due to the rise of the atmospheric temperature, under the condition of high ice content, a sliding soil body appears as a mixture of hard rock blocks and liquid slurry, and is easy to generate a sliding plane approximately parallel with the slope face. For example, in a region between WUdaoliang and Tuotuohe near the milestone of the K3035 mileage segment of the Qinghai-Tibet highway, with the overall slope of about 7°, a topical thaw-slumping phenomenon with the longitudinal direction of 95 m and the maximum width of 72 m occurs. Hence, it is important to develop the studies on the thaw-slumping characteristics and mechanism of low-angle side slopes.

The document "Study on Model Experiment of Thaw Slumping in Permafrost Region of Qinghai-Tibet Plateau" (Jin Dewu, et al. Engineering Investigation, 2006, 9: 1-6) designed a physical model (compressed at a scale of 1:10) similar to the geometry and slope structure of the thaw-slumping body of the K3035 mileage segment of the Qinghai-Tibet highway, and the testing process was divided into several links of ice box processing and ice layer fabrication, soil sample rolling and preparation; correction and calibration of monitoring instruments, fabrication of a slope scale model in a model box and instrument embedment; and a special ice layer was used in the test process for the temperature control, the temperature was set at −1° C., the other one was used for controlling the temperature of the soil body, total four freezing-thawing periodic cycles were completed, and based on pre-embedded common temperature probes, displacement sensors and extensimeters, the displacement field and the temperature field of the side slop could be measured. However, conventional soil body deformation measurement method is to embed a series of sensors inside the soil body, and obtain the displacements of some discrete points, the sensors are easily subjected to the effect due to the disturbance of the external environment, the measurement result often are not accurate, and the whole displacement field in continuous deformation inside the soil body can not be presented as well. Modern digital image technologies are only limited to measure the macroscopic or boundary deformation of the soil body as well, and can not realize the visualization of the internal deformation of the soil body; and although X-ray, γ-ray, computer assisted tomographic scanning (CAT scanning) and magnetic resonance imaging technology (MRI) can be used for measuring the continuous deformation inside the soil body, and expensive expenses limit wide application of these technologies.

Controlled blasting is a blasting technique, which controls public hazards of frying objects, earthquake, air shock wave, fume, noise and so on generated due to the explosion of an object to be blasted by explosive by certain technical means, and has wide application in the engineering construction, for example, directional blasting, presplitting blasting, smooth surface blasting, rock plug blasting, millisecond controlled blasting; demolition blasting, static blasting, casting-filling blasting, weakly loose blasting, combustion agent blasting and the like. The directional blasting is a blasting technique, which utilizes the explosion action of explosive, to throw earth and stone of a certain region to a specified region and approximately stack into a required shape, is mainly used for repairing dams (water dams or tailing dams), building roads (road embankments and roadbeds), and leveling land (industrial lands and farmland construction), and is particularly suitable for work points of labor shortage, inconvenient transportation and no construction yard.

Document 1 "Study on Frozen Soil Blasting Crater and Model Test Of Frozen Soil Blastability" (Ma Qinyong. Journal of China Coal Society, 1997, 22(3): 288-293.) disclosed a program for the blasting crater model tests of frozen clay and sandy soil at different temperatures; document 2 "Preliminary Study on Blasting Parameters for Shaft Excavation in Frozen Soil" (Zong Qi, Yang Lujun, Engineering blasting, 1999, 5(2): 25-29.), and document 3 "Study of Smooth Blasting in Frozen Soil of the Shaft by Simulation" (Jiang Yusong, Journal of Huainan Institute of Technology) (2001, 21(4): 31-34.) disclosed a program for cutting blasting and smooth blasting model tests of frozen sandy soil; and Document 4 "A Study on Blasting Tests and Methods for Permafrost and Artificially Frozen Soils" (Ma Qinyong, Journal of Civil Engineering, 2004, 37(9): 75-78.) comprehensively introduced the research developments and achievements of blasting craters, cutting blasting and smooth blasting tests of frozen soil. These model test programs are all based on conventional test means, and are incapable of effectively acquiring specific fracture morphologies of frozen soil after the blasting tests. However, conventional soil body deformation measurement method is to embed a series of sensors inside the soil body, and obtain the displacements of some discrete points, the sensors are easily subjected to the effect due to the disturbance of the external environment, the measurement result often are not accurate, and the whole displacement field in continuous deformation inside the soil body can not be presented as well. Modern digital image technologies are only limited to measure the macroscopic or boundary deformation of the soil body as well, and can not realize the visualization of the internal deformation of the soil body; and although X-ray, γ-ray, computer assisted tomographic scanning (CAT scanning) and magnetic resonance imaging technology (MRI) can be used for measuring the continuous deformation inside the soil body, and expensive expenses limit wide application of these technologies.

Artificial synthesis of transparent soil in combination with optical observation and image processing techniques is utilized to realize the visualization of the internal deformation of the soil body, with low expense, and simple operation, and can be widely applied in model tests in the aspect of the geotechnical engineering, to study the internal law and mechanism of the soil body, which is of great significance on the research of the problem inherence of the geotechnical engineering. Its precondition is to obtain an artificially synthesized transparent soil with high transparency, and the properties similar to natural soil body. At present, different materials were adopted to prepare transparent soil, and some achievements were obtained. However, existing technical data show that, solid particles for preparing transparent soil mainly adopt quartz materials, with the refractive index themselves of the solid particles between 1.44-1.46, and adopt borosilicate glass materials, with the refractive index themselves of the solid particles between 1.46-1.48, which is far higher than the refractive index of water of 1.33 and that of ice of 1.31. Hence, the utilization of existing solid particles for preparing transparent soil is incapable of preparing a saturated transparent frozen soil sample.

The fluorine-containing polymer is Teflon AF 1600 produced by American DuPont Company (i.e. poly[4,5-difluoro-2,2bis(trifluoromethyl)-1,3-dioxole-co-tetrafluoro ethylene]), with the refractive index of 1.31, and the density of 2.1-2.3 g/cm$^3$; and it has the characteristics of high temperature resistance, low temperature resistance, chemical corrosion resistance, no viscosity, no toxicity, no pollution, high transparency and low refractive index, and also has the characteristics of gas permeability structure, hydrophobicity and chemical inertness, and has good similarity with the properties of natural soil body. Teflon AF 1600 (i.e. poly[4,5-difluoro-2,2bis(trifluoromethyl)-1,3-dioxole-co-tetrafluoroethylene]) can be dissolved in fluorine solvents, and can be formed into a film or formed by fusion compression; and at present, it is mainly used in coating and impregnation or made into fibers, and the prepared liquid core also has application in various fields of absorption, fluorescence, Raman spectral analysis, gas sensors and the like. The fluorine-containing polymer has high transparency, and the refractive index the same as ice, thus can be used as a transparent solid material in the preparation of transparent frozen soil.

SUMMARY OF THE INVENTION

Objective of the invention: in order to solve technical problems existing in the prior art, the present invention provides a transparent frozen soil and preparation method and application thereof, and the prepared transparent frozen soil can well simulate the properties of natural transparent frozen sandy soil.

The technical content: in order to realize the above technical objective, the present invention provides a transparent frozen soil, characterized in that it is prepared from a fluorine-containing polymer, ice particles and a colorless pore fluid by steps of preparing materials, blending, vacuuming, and freezing, and the dosages of said fluorine-containing polymer, ice particles and colorless pore fluid are calculated by test conditions and sample sizes; said colorless pore fluid is water, said fluorine-containing polymer is particles with the particle diameter of 0.25-2.0 mm, and its particles have irregular shape, and are Teflon AF 1600 produced by American DuPont Company (i.e. poly[4,5-difluoro-2,2bis(trifluoromethyl)-1,3-dioxole-co-tetrafluoro ethylene]), with the refractive index of 1.31, and the density of 2.1-2.3 g/cm$^3$; the particle diameter of said ice particle is 0.1-0.5 mm; the physical properties of said transparent frozen soil are: density of 1.53-2.0 g/cm$^3$, unit weight of 15-20 kN/m$^3$, and relative density 20-80%; and the mechanical properties are: internal friction angle of 30°-31°, elastic modulus of 8-61 MPa, and Poisson's ratio of 0.2-0.4.

Preferably, said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%.

In order to reduce the effect on the refractive index, said water is purified water.

The invention also provides a production method for the above transparent frozen soil, characterized in that it includes the following steps:

(1) material preparation: the dosages of the fluorine-containing polymer, the ice particles and the colorless pore fluid are calculated according to the test conditions and sample size dimensions; said fluorine-containing polymer is particles with the particle diameter of 0.25-2.0 mm, and is subjected to impurity cleaning and oven dried, and its particles have irregular shape, and are Teflon AF 1600 produced by American DuPont Company (i.e. poly[4,5-difluoro-2,2bis(trifluoromethyl)-1,3-dioxole-co-tetrafluoro ethylene]), with the refractive index of 1.31, and the density of 2.1-2.3 g/cm$^3$; said ice particles are obtained by mashing a frozen whole ice block, with the particle diameter of 0.1-0.5 mm; and the colorless pore fluid is water;

(2) blending: in a −6.0° C. to −8.0° C. cryogenic laboratory, firstly the fluorine-containing polymer and the ice particles are stirred uniformly, and loaded into a mold by 2-3 batches for the preparation of a sample, and compacted layer by layer; then water is added into the mold, and fills gaps between the fluorine-containing polymer particles and the ice particles;

(3) vacuuming: a vacuuming device is utilized to remove bubbles residual inside the sample, so that the sample reaches a fully saturated state; and (4) freezing: the sample is loaded in a −20° C. cryogenic box for freezing for 48 h, so as to prepare a transparent frozen soil simulating saturated frozen sandy soil, the physical properties of which are: density of 1.53-2.0 g/cm$^3$, unit weight of 15-20 kN/m$^3$, and relative density 20-80%; and the mechanical properties are: internal friction angle of 30°-31°, elastic modulus of 8-61 MPa, and Poisson's ratio of 0.2-0.4.

Preferably, said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%.

The present invention further provides application of the above transparent frozen soil in the frozen soil directional blasting model test.

The above application comprises the following processes:

(1) modeling: according to the test requirements and the natural frozen soil side slope model dimensions, a transparent model tank and a transparent frozen soil side slope model simulating the natural frozen soil side slope model are made, respectively, said transparent frozen soil side slope model is made of transparent frozen soil, and reserved with blast holes; and said transparent model tank is made of transparent toughened glass;

(2) mounting; the transparent frozen soil side slope model is loaded into the transparent model tank, and according to the test design, detonators and explosive are loaded in the reserved blast holes; and digital cameras capable of observing the space of the whole transparent model tank are arranged on the front view face, the side view face and the top view face outside the transparent model tank, and the digital cameras are connected with a processing device via data lines;

(3) testing: the detonators and explosive are detonated, the process of the directional blasting of the transparent frozen soil side slope model to form an artificial side slope is observed and recorded by the digital cameras, and the recorded data are sent to the processing device by data lines; and (4) process (1)-process (3) are repeated, the directional blasting processes of the transparent frozen soil side slope model under the conditions of different natural side slop heights, different blast hole diameters and depths and different explosive dosages can be observed by the processing device, so as to analyze the frozen soil directional blasting mechanism, and complete the directional blasting test of the frozen soil side slop model.

The present invention more further provides application of the above transparent frozen soil in the thawing-slumping test of the frozen soil road embankment model.

The above application comprises the following steps:

(1) modeling: according to the test requirements and frozen soil road embankment model dimensions a transparent model tank and a transparent frozen soil road embankment model simulating a frozen soil road embankment model are made, respectively, said transparent frozen soil road embankment model is made of the transparent frozen soil material, and pre-embedded with temperature sensors; and said transparent model tank is made of organic glass;

(2) mounting; in a cryogenic laboratory, the transparent frozen soil road embankment model is loaded into the transparent model tank, and a heating source is mounted on the transparent model tank, and above the adret face of the transparent frozen soil road embankment model; outside the transparent model tank, one side parallel to the cross section of the transparent frozen soil road embankment model is provided with a laser source, and one side perpendicular to the cross section of the transparent frozen soil road embankment model is provided with a digital camera, and the digital camera and the temperature sensor are connected with the processing device via data lines; and the axial line of said digital camera is perpendicular to that of said laser source, and the intersection point of the axial line of said digital camera and that of said laser source is located inside said transparent model tank; and (3) testing: the laser source is turned on, the brightness of the tangent plane of particles formed inside the transparent frozen soil road embankment model is inspected, and the laser angle is adjusted, so that the laser is perpendicularly incident onto the tangent plane, and through the middle position of the longitudinal direction of the transparent frozen soil road embankment model; the digital camera is turned on, and the lens of the digital camera is adjusted, so that it can cover the adret face and the ubac face of the transparent frozen soil road embankment model; i.e. the laser source irradiates the cross section of the transparent frozen soil road embankment model, and the cross section of the transparent frozen soil road embankment model irradiated by the laser source is recorded by the digital camera; and according to the experiment design, the heating source is intermittently turned on, the thawing-slumping process of the adret face of the transparent frozen soil road embankment model under the periodic cycle of freezing and thawing is observed and recorded by the digital camera, and the recorded data are sent to the processing device via a data line.

In step (2), the adret face is laid with thereon a thermal insulating material, and the toe position of the adret face is provided with a bridge wall; said thermal insulating material is a broken stone layer simulated by fluorine-containing polymer particles with the thickness of 5-15 mm or a polyethylene foamed plastic mesh, and said bridge wall is made of organic glass; and in step (3), according to the experiment design, the heating source is intermittently turned on, the thawing-slumping process of the adret face of the transparent frozen soil road embankment model under the periodic cycle of freezing and thawing is observed and recorded by the digital camera, the recorded data are sent to the processing device via a data line, and the effect of treatment measures on the elimination of the thawing-slumping phenomenon is examined.

The beneficial effect: compared with the prior art, the present invention adopts fluorine-containing polymer Teflon AF 1600 (i.e. poly[4,5-difluoro-2,2bis(trifluoromethyl)-1,3-dioxole-co-tetrafluoroethylene]) with the refractive index the same as ice, ice particles and water to prepare a transparent frozen soil, the prepared one has good similarity with the properties of the natural frozen soil body, can widely substitute natural frozen sandy soil, well simulates the properties of natural transparent frozen soil, is effectively used in model tests in the geotechnical engineering, including the simulation of frozen soil directional blasting and thaw slumping, with accurate measurement results, and can realize the visualization of the internal deformation of a soil body, and it is low in the expense, and simple in the operation.

PARTICULAR EMBODIMENTS

Figure 1:
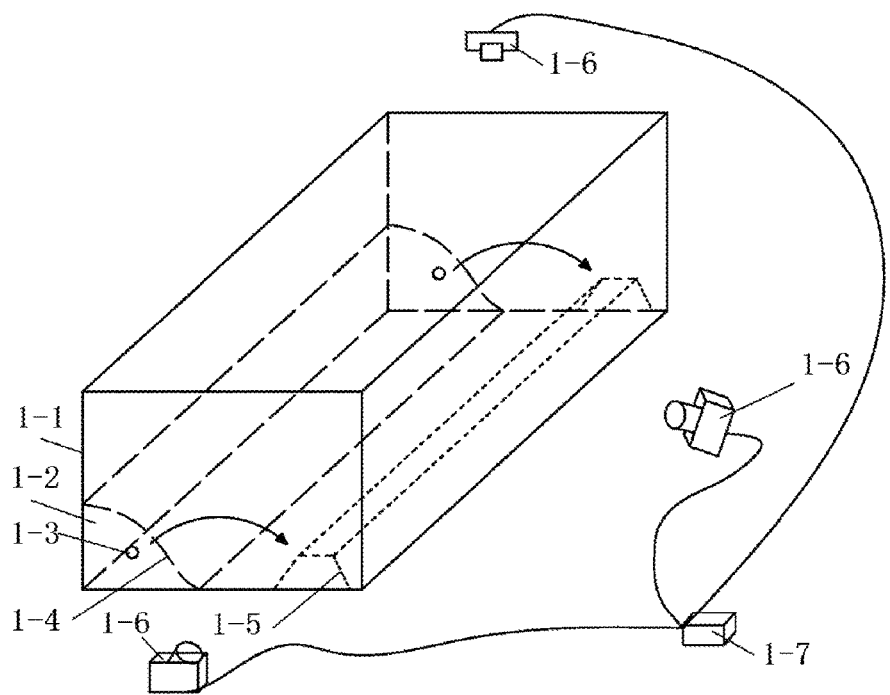
FIG. 1 A schematic diagram of a frozen soil side slope model directional blasting test device.
Figure 2:
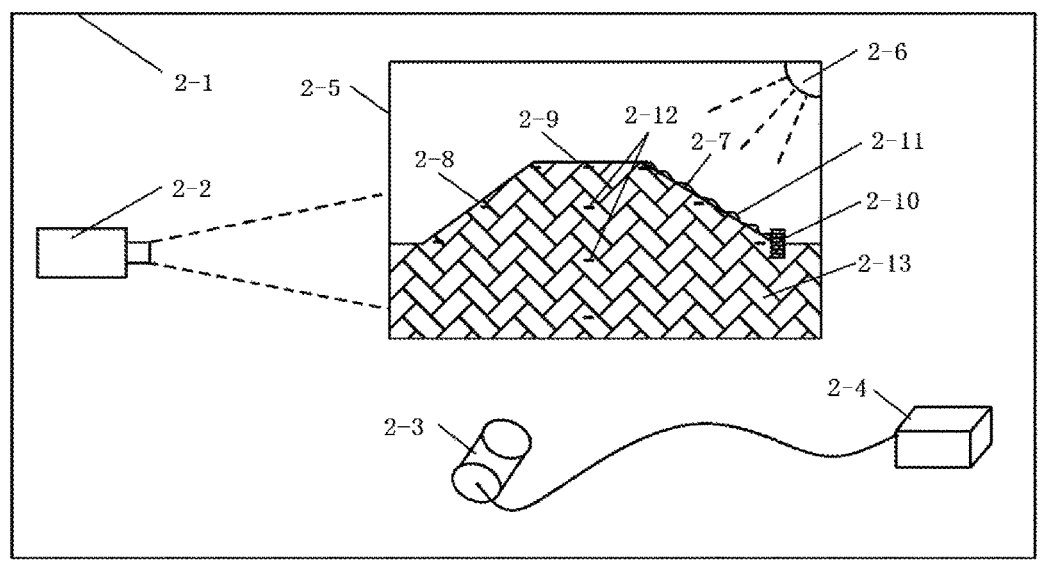
FIG. 2 A schematic diagram of a frozen soil road embankment model thaw-slumping test device.

Example 1 Preparation of Transparent Frozen Soil

Application of a fluorine-containing polymer in the preparation of a transparent frozen soil: it is used as a transparent solid material while in the preparation of a transparent frozen soil, said fluorine-containing polymer is particles with the particle diameter of 0.25-2.0 mm, and its particles have irregular shape, and are Teflon AF 1600 produced by American DuPont Company (i.e. poly[4,5-difluoro-2,2bis(trifluoromethyl)-1,3-dioxole-co-tetrafluoroethylene]), with the refractive index of 1.31, and the density of 2.1-2.3 g/cm$^3$.

A production method for the preparation of a transparent frozen soil from the above fluorine-containing polymer comprises the following steps:

(1) material preparation: the dosages of the fluorine-containing polymer, the ice particles and the colorless pore fluid are calculated according to the test conditions and the sample size dimensions; said fluorine-containing polymer is particles with the particle diameter of 0.25-2.0 mm, and is subjected to impurity cleaning and oven dried, and its particles have irregular shape, and are Teflon AF 1600 produced by American DuPont Company (i.e. poly[4,5-difluoro-2,2bis(trifluoromethyl)-1,3-dioxole-co-tetrafluoro-ethylene]), with the refractive index of 1.31, and the density of 2.1-2.3 g/cm$^3$; said fluorine-containing polymer particles with the particle diameter greater than or equal to 0.25 mm and smaller than 0.5 mm account for 20%, those with the particle diameter greater than or equal to 0.5 mm and smaller than 1.0 mm account for 30%, those with the particle diameter greater than or equal to 1.0 mm and smaller than 1.5 mm account for 30%, those with the particle diameter greater than or equal to 1.5 mm and smaller than 2.0 mm account for 20%, in terms of weight, the sum is 100%, and they are mixed uniformly; said ice particles are obtained by mashing a frozen whole ice block, with the particle diameter of 0.1-0.5 mm; and the colorless pore fluid is water, and in order not to affect the refractive index, said water is purified water;

the dosages of the fluorine-containing polymer, the ice particles and the colorless pore fluid are calculated according to the test conditions and the sample size dimension;

the sample of the example has the water content of 100.0%, the dry density of 0.55 g/cm$^3$, and the sample size (height of 125.0 mm and diameter of 61.8 mm), the temperature of the cryogenic laboratory is of −6.0° C., the mass of the fluorine-containing polymer particles (the mass of particles=dry density×sample volume) required for preparing a sample is calculated to be 206.0 g, and the total water content (water content of 100.0%, and the mass of the total water content is equal to the mass of particles) is 206.0 g; and since sandy soil has the non-frozen water content about 15% when the temperature is at −6.0° C., the mass of purified water added in the preparation process of the sample should be 30.9 g, and the mass of the ice particles is 175.1 g;

(2) blending: in the −6.0° C. cryogenic laboratory, firstly the fluorine-containing polymer particles and the ice particles determined in step (1) are stirred uniformly, loaded into a mold by 3 batches for the preparation of a sample, and compacted layer by layer, to 70% of the designed relative density; then purified water is added into the mold, and fills gaps between the fluorine-containing polymer particles and the ice particles;

(3) vacuuming: a vacuuming device is utilized to remove bubbles residual inside the sample, so that the sample reaches a fully saturated state; and (4) freezing: the sample is loaded in a −20° C. cryogenic box and frozen for 48 h, so as to prepare a transparent frozen soil simulating saturated frozen sandy soil, the physical properties of which are: density of 1.9 g/cm$^3$, unit weight of 19 kN/m$^3$, and relative density 70%; and the mechanical properties are: internal friction angle of 31°, elastic modulus of 40 MPa, and Poisson's ratio of 0.3.

Said transparent frozen soil of the example can be used for simulating saturated frozen sandy soil.

Example 2 Preparation of Transparent Frozen Soil

The preparation steps are the same as those of the example 1, and the difference is, in step (1), fluorine-containing polymer particles of the density of 2.1 g/cm$^3$ are selected, fluorine-containing polymer particles with the particle diameter greater than or equal to 0.25 mm and smaller than 0.5 mm account for 20%, those with the particle diameter greater than or equal to 0.5 mm and smaller than 1.0 mm account for 30%, those with the particle diameter greater than or equal to 1.0 mm and smaller than 1.5 mm account for 30%, those with the particle diameter greater than or equal to 1.5 mm and smaller than 2.0 mm account for 20%, in terms of weight, the sum is 100%, and they are mixed uniformly;

in step (2), the relative density is controlled at 30%; and the physical properties of the transparent frozen soil prepared by the example are: density of 1.82 g/cm$^3$, unit weight of 18 kN/m$^3$, and relative density 30%; and the mechanical properties are: internal friction angle of 30°, elastic modulus of 10 MPa, and Poisson's ratio of 0.35.

Said transparent frozen soil of the example can be used for simulating saturated frozen sandy soil.

Example 3 Application of Application of the Transparent Frozen Soil in the Frozen Soil Directional Blasting Model Test A frozen soil side slope directional blasting test device, comprises the transparent model tank 1-1, the transparent model tank 1-1 is provided with therein the transparent frozen soil side slope model 1-2 simulating the natural side slope 1-4, the transparent frozen soil side slope model 1-2 is sequentially provided with therein blast holes 1-3, and the blast holes 1-3 are provided with therein explosive and detonators; the digital cameras 1-6 capable of observing the space of the whole transparent model tank 1-1 are arranged on the front view face, the side view face and the top view face outside the transparent model tank 1-1, and the digital cameras 1-6 are connected with a processing device 1-7 via data lines; and while in the directional blasting, the process of the directional blasting of the transparent frozen soil side slope model 1-2 to form the artificial side slope 1-5 under the conditions of different natural side slop 1-4 heights, different blast hole diameters and depths and different explosive dosages is observed by the digital cameras 1-6, and the recorded data are sent to the processing device 1-7, so as to complete the directional blasting test of the frozen soil side slop model. Said transparent model tank 1-1 of the present invention is made of transparent toughened glass.

Said transparent frozen soil side slope model 1-2 of the present invention is made of the transparent frozen soil material prepared by the example 1 and example 2 in a transparent model tank with the required dimensions.

Said digital cameras 1-6 of the present invention are high-resolution high-speed digital cameras, with the resolution of 50-500 w (500 w is adopted in the present invention), frame exposure, the frame number of 25, and the exposure time of 10 μs-10 s (10 μs is adopted in the present invention).

The frozen soil side slope model directional blasting test method comprises the following processes:

(1) modeling: according to the test requirement and the natural frozen soil side slope model dimensions, the transparent model tank 1-1 and the transparent frozen soil side slope model 1-2 simulating the natural frozen soil side slope model are made, respectively, said transparent frozen soil side slope model 1-2 is made of transparent frozen soil, and reserved with blast holes 1-3; and said transparent model tank 1-1 is made of transparent toughened glass; and firstly a mold simulating the natural side slope model is fabricated according to the test requirements, and the dosages of the fluorine-containing polymer, the ice particles and the colorless pore fluid are calculated according to the test conditions and mold size dimensions; and the example adopts the conditions of the example 1 for preparing the transparent froze soil to prepare a transparent frozen soil, and obtains the transparent frozen soil side slope model 1-2 simulating the natural frozen soil side slope model;

(2) mounting; the transparent frozen soil side slope model 1-2 is loaded into the transparent model tank 1-1, and according to the test design, detonators and explosive are loaded in the reserved blast holes 1-3, and the dosage of the explosive is determined according to the test design; digital cameras 1-6 capable of observing the space of the whole transparent model tank 1-1 are arranged on the front view face, the side view face and the top view face outside the transparent model tank 1-1, and the digital cameras 1-6 are connected with a processing device 1-7 via data lines; and said digital cameras 1-6 of the present invention are high-resolution high-speed digital cameras, with the resolution of 500 w, frame exposure, the frame number of 25, and the exposure time of 10 μs; and (3) testing: the detonators and explosive are detonated, the process of the directional blasting of the transparent frozen soil side slope model 1-2 to form an artificial side slope is observed and recorded by the digital cameras 1-6, and the recorded data are sent to the processing device 1-7 by data line; and in the test, the PIV technology (Particle Image Velocimetry) in combination with image processing software PIVview2C is utilized to process the picture data acquired by the numeral cameras 1-6; and (4) process (1)-process (3) are repeated, the directional blasting processes of the transparent frozen soil side slope model 1-2 under the conditions of different natural side slop 1-4 heights, different blast hole 1-3 diameters and depths and different explosive dosages can be observed by the processing device 1-7, so as to analyze the frozen soil directional blasting mechanism, and complete the directional blasting test of the frozen soil side slop model 1-2.

Example 4 Application of the Transparent Frozen Soil in the Thawing-Slumping Test of the Frozen Soil Road Embankment Model A frozen soil road embankment thaw-slumping test device, comprises the cryogenic laboratory 2-1, the cryogenic laboratory 2-1 is provided with therein the transparent model tank 2-5, the transparent model tank 2-5 is provided with therein the transparent frozen soil road embankment model 2-13 simulating the road embankment 2-9, the transparent frozen soil road embankment model 2-13 is pre-embedded with therein a temperature sensor 2-12, and the adret face of the road embankment 2-9 is provided with thereabove the heating source 2-6 mounted on the transparent model tank 2-5; the adret face 2-7 is laid with thereon the thermal insulating material 2-11, and the toe position of the adret face 2-7 is provided with the bridge wall 2-10; outside the transparent model tank 2-5, one side parallel to the cross section of the transparent frozen soil road embankment model 2-13 is provided with the laser source 2-2 (disposed at one side of the ubac face 2-8 in the example), and one side perpendicular to the cross section of the transparent frozen soil road embankment model 2-13 is provided with the digital camera 2-3, and the digital camera 2-3 and the temperature sensor 2-12 are connected with the processing device 2-4 via a data line; the axial line of said digital camera 2-3 is perpendicular to that of said laser source 2-2, and the intersection point of the axial line of said digital camera 2-3 and that of said laser source 2-2 is located inside said transparent model tank 2-5; and he laser source 2-2 irradiates the cross section of the transparent frozen soil road embankment model 2-13, and the cross section of the transparent frozen soil road embankment model 2-13 irradiated by the laser source 2-2 is recorded by the digital camera 2-3.

Said transparent frozen soil road embankment model 2-13 of the present invention is made of the transparent frozen soil, the dosages of the fluorine-containing polymer, the ice particles and purified water are calculated according to the test conditions and the sample size dimensions in the mold, and the transparent frozen soil road embankment model 2-13 is prepared in the mold by adopting the method of the example 2 for preparing the transparent frozen soil.

When the slope angles of the adret face 2-7 and the ubac face 2-8 are greater than 4°-9°, the possibility of the occurrence of thaw slumping exists. The slope angle of the adret face 2-7 of the transparent frozen soil road embankment model 2-13 prepared by the example is 31°, and that of the ubac face 2-8 is 36°.

Said transparent model tank 2-5 and the bridge wall 2-10 of the present invention are made of organic glass; and said thermal insulating material 2-11 is a broken stone layer simulated by fluorine-containing polymer particles with the thickness of 5-15 mm or a polyethylene foamed plastic mesh.

Said heating source 2-6 of the present invention is a linear heating resistance wire, and the maximum temperature near the resistance wire can be up to 25-28° C.

Said laser source 2-2 of the present invention is an intracavity-type helium-neon laser device, and the power can be 50-500 mW (500 m W in the example).

Said digital cameras 1-6 of the present invention are high-resolution high-speed digital cameras, with the resolution of 50-500 w (500 w in the example), frame exposure, frame number of 25, and exposure time of 10 μs-10 s (10 μs in the example).

Particularly, the frozen soil road embankment model thaw-slumping test method comprises the following processes:

(1) modeling: the transparent model tank 2-5 and the transparent frozen soil road embankment model 2-3 simulating the frozen soil road embankment model are made, respectively according to the test requirement and frozen soil road embankment model dimensions, said frozen soil road embankment model 2-13 is made of the transparent frozen soil material, and pre-embedded with the temperature sensor 2-12; and said transparent model tank2-5 is made of organic glass;

(2) mounting; in the cryogenic laboratory 2-1, the transparent frozen soil road embankment model 2-13 is loaded into the transparent model tank 2-5, and the heating source 2-6 is mounted on the transparent model tank 2-5, and above the adret face 2-7 of the transparent frozen soil road embankment model 2-13; outside the transparent model tank 2-5, one side parallel to the cross section of the transparent frozen soil road embankment model 2-13 is provided with the laser source 2-2 (disposed at one side of the ubac face 2-8 in the example), and one side perpendicular to the cross section of the transparent frozen soil road embankment model 2-13 is provided with the digital camera 2-3, and the digital camera 2-3 and the temperature sensor 2-12 are connected with the processing device 2-4; the axial line of said digital camera 2-3 is perpendicular to that of said laser source 2-2, and the intersection point of the axial line of said digital camera 2-3 and that of said laser source 2-2 is located inside said transparent model tank 2-5; and said heating source 2-6 of the present invention is a linear heating resistance wire, and the maximum temperature near the resistance wire can be up to 25-28° C.

Said laser source 2-2 of the present invention is an intracavity-type helium-neon laser device, and the power can be 50-500 mW (500 m W in the example).

Said digital cameras 1-6 of the present invention are high-resolution high-speed digital cameras, with the resolution of 50-500 w (500 w in the example), frame exposure, frame number of 25, and exposure time of 10 μs-10 s (10 μs in the example).

(3) testing: the laser source 2-2 is turned on, the brightness of the tangent plane of particles formed inside the transparent frozen soil road embankment model 2-13 is inspected, and the laser angle is adjusted, so that the laser is perpendicularly incident onto the tangent plane, and through the middle position of the longitudinal direction of the transparent frozen soil road embankment model 2-13; the digital camera 2-3 is turned on, and the lens of the digital camera 2-3 is adjusted, so that it can cover the adret face 2-7 and the ubac face 2-8 of the transparent frozen soil road embankment model 2-13; i.e. the laser source 2-2 irradiates the cross section of the transparent frozen soil road embankment model 2-13, and the cross section of the transparent frozen soil road embankment model 2-13 irradiated by the laser source is recorded by the digital camera 2-3; and according to the experiment design, the heating source 2-6 is intermittently turned on, the thawing-slumping process of the adret face 2-7 of the transparent frozen soil road embankment model 2-13 under the periodic cycle of freezing and thawing is observed and recorded by the digital camera 2-3, and the recorded data are sent to the processing device 2-4 via a data line.

In the test, the PIV technology (Particle Image Velocimetry) in combination with image processing software PIVview2C is utilized to process the picture data acquired by the numeral cameras 1-6; and in order to examine the effect of treatment measures on the elimination of the thaw-slumping phenomenon, the adret face is laid with therein the thermal insulating material 2-11, and the toe position of the adret face is provided with the bridge wall 2-10; said thermal insulating material 2-11 is a broken stone layer simulated by fluorine-containing polymer particles with the thickness of 5-15 mm or a polyethylene foamed plastic mesh (a broken stone layer simulated by fluorine-containing polymer particles with the thickness of 10 mm in the example), and said bridge wall is made of organic glass; and in step (3), according to the experiment design, the heating source 2-6 is intermittently turned on, the thawing-slumping process of the adret face 2-7 of the transparent frozen soil road embankment model 2-13 under the periodic cycle of freezing and thawing is observed and recorded by the digital camera 2-3, the recorded data are sent to the processing device 2-4 via a data line, and the effect of treatment measures on the elimination of the thawing-slumping phenomenon is examined.

The invention claimed is:

1. A transparent frozen soil, wherein the transparent frozen soil is prepared from a fluorine-containing polymer, ice particles and a colorless pore fluid by steps of preparing materials, blending, vacuuming, and freezing, and the dosages of said fluorine-containing polymer, ice particles and colorless pore fluid are calculated by the test conditions and the sample sizes; said colorless pore fluid is water, said fluorine-containing polymer is particles with the particle diameter of 0.25-2.0 mm, and its particles have irregular shape, and is poly[4,5-difluoro-2,2bis(trifluoromethyl)-1,3-dioxole-co-tetrafluoroethylene], with the refractive index of 1.31, and the density of 2.1-2.3 g/cm$^3$; the particle diameter of said ice particle is 0.1-0.5 mm; the physical properties of said transparent frozen soil are: density of 1.53-2.0 g/cm$^3$, unit weight of 15-20 kN/m$^3$, and relative density 20-80%; and the mechanical properties are: internal friction angle of 30°-31°, modulus of 8-61 MPa, and Poisson's ratio of 0.2-0.4.

2. The transparent frozen soil according to claim 1, wherein said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%.

3. The transparent frozen soil according to claim 1, wherein said water is purified water.

4. A production method for the transparent frozen soil according to claim 1, wherein the production method includes the following steps:
   (1) material preparation: the dosages of the fluorine-containing polymer, the ice particles and the colorless pore fluid are calculated according to the test conditions and the sample size dimensions; said fluorine-containing polymer is particles with the particle diameter of 0.25-2.0 mm, and is subjected to impurity cleaning and oven dried, and its particles have irregular shape, and is poly[4,5-difluoro-2,2bis(trifluoromethyl)-1,3-dioxole-co-tetrafluoroethylene], with the refractive index of 1.31, and the density of 2.1-2.3 g/cm$^3$; said ice particles are obtained by mashing a frozen whole ice block, with the particle diameter of 0.1-0.5 mm; and said colorless pore fluid is water;
   (2) blending: in a −6.0° C. to −8.0° C. cryogenic laboratory, firstly the fluorine-containing polymer and the ice particles are stirred uniformly, and loaded into a mold by 2-3 batches for the preparation of a sample, and compacted layer by layer; then water is added into the mold, and fills gaps between the fluorine-containing polymer particles and the ice particles;
   (3) vacuuming: a vacuuming device is utilized to remove bubbles residual inside the sample, so that the sample reaches a fully saturated state; and
   (4) freezing: the sample is loaded in a −20° C. cryogenic box and frozen for 48 h, so as to prepare a transparent frozen soil simulating saturated frozen sandy soil, the physical properties of which are: density of 1.53-2.0 g/cm$^3$, unit weight of 15-20 kN/m$^3$, and relative density 20-80%; and the mechanical properties are: internal friction angle of 30°-31°, elastic modulus of 8-61 MPa, and Poisson's ratio of 0.2-0.4.

5. The production method of said transparent frozen soil according to claim 4, wherein in step (1), said fluorine-containing polymer particles with the particle diameter greater than or equal to 0.25 mm and smaller than 0.5 mm account for 10-50%, those with the particle diameter greater than or equal to 0.5 mm and smaller than 1.0 mm account for 10-50%, those with the particle diameter greater than or equal to 1.0 mm and smaller than 1.5 mm account for 10-50%, those with the particle diameter greater than or equal to 1.5 mm and smaller than 2.0 mm account for 10-50%, and in terms of weight, the sum is 100%.

6. Application of said transparent frozen soil according to claim 1 in a frozen soil directional blasting model test, comprising the following steps:

(1) modeling: according to the test requirements and the natural frozen soil side slope model dimensions, a transparent model tank and a transparent frozen soil side slope model simulating the natural frozen soil side slope model are made, respectively, said transparent frozen soil side slope model is made of transparent frozen soil, and reserved with blast holes; and said transparent model tank is made of transparent toughened glass;

(2) mounting: the transparent frozen soil side slope model is loaded into the transparent model tank, and according to the test design, detonators and explosive are loaded in the reserved blast holes; and digital cameras capable of observing the space of the whole transparent model tank are arranged on the front view face, the side view face and the top view face outside the transparent model tank, and the digital cameras are connected with a processing device via data lines;

(3) testing: the detonators and explosive are detonated, the directional blasting of the transparent frozen soil side slope model to form an artificial side slope is observed and recorded by the digital cameras, and the recorded data are sent to the processing device by data lines; and (4) step (1)-step (3) are repeated, the directional blasting of the transparent frozen soil side slope model under the conditions of different natural side slop heights, different blast hole diameters and depths and different explosive dosages can be observed by the processing device, so as to analyze the directional blasting mechanism of the frozen soil, and complete the directional blasting test of the frozen soil side slop model.

7. Application of transparent frozen soil according to claim 1 in a thawing-slumping test of the frozen soil road embankment model, comprising the following steps:

(1) modeling: according to the test requirements and frozen soil road embankment model dimensions the transparent model tank and the transparent frozen soil road embankment model simulating the frozen soil road embankment model are made, respectively, said transparent frozen soil road embankment model is made of the transparent frozen soil material, and pre-embedded with temperature sensors; and said transparent model tank is made of organic glass;

(2) mounting; in a cryogenic laboratory, the transparent frozen soil road embankment model is loaded into the transparent model tank, and a heating source is mounted on the transparent model tank, and above the adret face of the transparent frozen soil road embankment model; outside the transparent model tank, one side parallel to the cross section of the transparent frozen soil road embankment model is provided with a laser source, and one side perpendicular to the cross section of the transparent frozen soil road embankment model is provided with a digital camera, and the digital camera and the temperature sensor are connected with the processing device via a data line; and the axial line of said digital camera is perpendicular to that of said laser source, and the intersection point of the axial line of said digital camera and that of said laser source is located inside said transparent model tank; and (3) testing: the laser source is turned on, the brightness of the tangent plane of particles formed inside the transparent frozen soil road embankment model is inspected, and the laser angle is adjusted, so that the laser is perpendicularly incident onto the tangent plane, and through the middle position of the longitudinal direction of the transparent frozen soil road embankment model; the digital camera is turned on, and the lens of the digital cameras is adjusted, so that it can cover the adret face and the ubac face of the transparent frozen soil road embankment model; the laser source irradiates the cross section of the transparent frozen soil road embankment model, and the cross section of the transparent frozen soil road embankment model irradiated by the laser source is recorded by the digital camera; and according to the experiment design, the heating source is intermittently turned on, the thawing-slumping process of the adret face of the transparent frozen soil road embankment model under the periodic cycle of freezing and thawing is observed and recorded by the digital cameras, and the recorded data are sent to the processing device via a data line.

8. The application according to claim 7, wherein in step (2), the adret face is laid with thereon a thermal insulating material, and the toe position of the adret face is provided with a bridge wall; said thermal insulating material is a broken stone layer simulated by fluorine-containing polymer particles with the thickness of 5-15 mm or a polyethylene foamed plastic mesh, and said bridge wall is made of organic glass; and in step (3), according to the experiment design, the heating source is intermittently turned on, the thawing-slumping process of the adret face of the transparent frozen soil road embankment model under the periodic cycle of freezing and thawing is observed and recorded by the digital cameras, the recorded data are sent to the processing device via a data line, and the effect of treatment measures on the elimination of the thawing-slumping phenomenon is examined.

* * * * *